United States Patent [19]

Sunshine et al.

[11] Patent Number: 6,037,592
[45] Date of Patent: *Mar. 14, 2000

[54] SYSTEM FOR MEASURING GASES DISSOLVED IN A LIQUID

[75] Inventors: Steven S. Sunshine, San Carlos; David C. Bliven, San Jose; John Seymour Mattis, Sunnyvale, all of Calif.

[73] Assignee: Underground Systems, Inc., Armonk, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/800,678

[22] Filed: Feb. 14, 1997

[51] Int. Cl.[7] .................................................. G01N 21/35
[52] U.S. Cl. ........................................... 250/343; 250/345
[58] Field of Search ....................... 250/339.03, 339.04, 250/339.13, 341.6, 343, 345

[56] References Cited

U.S. PATENT DOCUMENTS

| | | | |
|---|---|---|---|
| 3,228,394 | 1/1966 | Ayres | 128/142 |
| 4,058,373 | 11/1977 | Kurz et al. | 55/16 |
| 4,112,737 | 9/1978 | Morgan | 73/23 |
| 4,247,770 | 1/1981 | Welch | 250/253 |
| 4,293,399 | 10/1981 | Belanger et al. | 204/195 P |
| 4,444,040 | 4/1984 | Sakai et al. | 73/19 |
| 4,502,320 | 3/1985 | Sakai et al. | 73/23 |
| 4,542,640 | 9/1985 | Clifford | 73/23 |
| 4,654,806 | 3/1987 | Poyser et al. | 364/551 |

(List continued on next page.)

FOREIGN PATENT DOCUMENTS

| | | | |
|---|---|---|---|
| 0608049 A2 | 7/1994 | European Pat. Off. | G01N 21/61 |
| 2204332 | 8/1972 | Germany | G01N 25/18 |
| 218465 A1 | 2/1985 | Germany | G01N 21/35 |
| WO 93/18399 | 9/1993 | WIPO | G01N 33/00 |
| WO 93/20429 | 10/1993 | WIPO | G01N 21/35 |
| WO 95/28626 | 10/1995 | WIPO | G01N 1/00 |

OTHER PUBLICATIONS

Derwent Abstract WPI Acc No. 95–373884/48 (abstract of WO 95/28626 (1995), Medium Sensor GmbH).
Fenner et al., "IR Transform Spectrometer–On–A–Chip," Amer. Phys. Soc. meeting, San Jose, California, Mar. 1995.
Fenner et al., Appl. Phys. Lett. 62 (19), pp. 2428–2430 (May 1993).
Fenner et al., IEEE Trans. Appl. Superconductivity, vol. 3, No. 1, pp. 2104–2106 (Mar. 1993).
Fenner et al., "Epitaxial YBCO Bolometers on Silicon Windows," 4th Int. Superconductive Electron. Conf. (Aug. 1993).
Fenner et al., SPIE vol. 2159, pp. 10–20 (Jan. 1994).

*Primary Examiner*—David P. Porta
*Attorney, Agent, or Firm*—Frommer Lawrence & Haug, LLP; William S. Frommer

[57] ABSTRACT

A method and apparatus for continuously monitoring and measuring the concentration of gases in a gas-containing liquid such as a transformer oil. The method and apparatus employ a passive gas extraction technique which comprises a high performance membrane material to extract dissolved gases from the oil, and an IR-based sensor to detect gases present. The passive gas extractor extracts dissolved gas from the gas-containing liquid, there being a known relationship between the concentration of a constituent gas in the extracted gas and the concentration of the constituent gas remaining dissolved in the gas-containing liquid. The gas sensor senses the concentration of a constituent gas in the extracted gas, in the presence of other constituent gases. The gas sensor comprises a sample chamber which receives the extracted gas, a non-dispersive infrared (IR) absorption sensing system which generates an electrical signal corresponding to the light absorption, at one or more specified IR wavelengths, of the extracted gas in the chamber, and an electrical output comprising the electrical signal generated by the non-dispersive IR absorption sensing system. A processor having receives the electrical signal corresponding to the light absorption, at the one or more specified IR wavelengths, of the extracted gas in the chamber, and computes the concentration of at least one gas constituent present in the extracted gas.

30 Claims, 7 Drawing Sheets

U.S. PATENT DOCUMENTS

| | | | |
|---|---|---|---|
| 4,764,344 | 8/1988 | Knab | 422/89 |
| 4,847,783 | 7/1989 | Grace et al. | 364/497 |
| 4,890,478 | 1/1990 | Claiborne et al. | 73/19 |
| 4,896,143 | 1/1990 | Dolnick et al. | 340/634 |
| 4,911,892 | 3/1990 | Grace et al. | 422/94 |
| 5,026,992 | 6/1991 | Wong | 250/343 |
| 5,049,742 | 9/1991 | Hosonuma et al. | 250/343 X |
| 5,051,114 | 9/1991 | Nemser et al. | 55/16 |
| 5,065,025 | 11/1991 | Doyle | 250/343 |
| 5,070,738 | 12/1991 | Morgan | 73/863.83 |
| 5,163,332 | 11/1992 | Wong | 73/862.23 |
| 5,222,389 | 6/1993 | Wong | 73/31.02 |
| 5,244,478 | 9/1993 | Jolly | 96/6 X |
| 5,258,310 | 11/1993 | Abe et al. | 436/60 |
| 5,339,672 | 8/1994 | Spicar | 73/19.1 |
| 5,400,641 | 3/1995 | Slemon et al. | 73/19.01 |
| 5,417,821 | 5/1995 | Pyke | 204/153.1 |
| 5,455,423 | 10/1995 | Mount et al. | 250/343 |
| 5,473,161 | 12/1995 | Nix et al. | 250/343 |
| 5,668,373 | 9/1997 | Robbat, Jr. et al. | 250/339.07 X |

SYSTEM FOR MEASURING GASES DISSOLVED IN A LIQUID

RELATED APPLICATIONS

This application is related to copending, commonly assigned application application Ser. No. 08/800,676, filed Feb. 14, 1997 (hereinafter "the '676 application") and copending, commonly assigned application application Ser. No. 08/798,283, filed Feb. 14, 1997, now U.S. Pat. No. 5,749,942 (hereinafter "the '942 patent") which are filed on the same day as this application, the entire disclosures of which are incorporated herein by reference for all purposes.

BACKGROUND OF THE INVENTION

1. Field of the Invention

This invention relates to sensor systems for measuring the concentration of gases dissolved in a liquid. In particular this invention relates to a sensor system which comprises a method and apparatus for measuring the concentration of dissolved gases in insulating and cooling oils used in electrical transformers.

2. Introduction to the Invention

Electrical transformers are known to degrade and fail due to age, high loads, varying loads, and environmental conditions. In some instances such failures can be catastrophic. It is also known that oils used for cooling and insulation of the transformers, as well as other insulation materials, e.g. cellulosic insulation (paper), can break down under the electrical and thermal stresses. The break down of the oil and other materials yields a variety of products, including certain gases which are often referred to as "fault gases." Such fault gases may include hydrogen ($H_2$), carbon monoxide (CO), carbon dioxide ($CO_2$), methane ($CH_4$), acetylene ($C_2H_2$), ethylene ($C_2H_4$), and ethane ($C_2H_6$), and other gases. The generation of fault gases can be accelerated by the presence of water which degrades the performance of the insulating fluid.

In many cases, the degradation and ultimate failure of a transformer may occur over a fairly long period of time. The detection of the fault gases can be useful in detecting degradation and/or failure of the transformer or its components. Thus, it has been found to be useful to periodically sample and analyze the transformer oil to identify the composition and, in some cases, the concentration of fault gases present in the oil, in order to thereby assess the health of the transformer.

However, the methods and equipment used to date are cumbersome and time consuming. Some methods require oil and/or gas samples be extracted at the transformer site and then taken to a laboratory for analysis. Some methods do not provide data on multiple gases of interest. Some systems which do provide data on multiple gases require that the various gases be separated prior to analysis. Most methods require that a carrier gas, such as nitrogen, be injected to facilitate the transportation of extracted gases though the sensing system. As a result of these limitations, the transformers are typically monitored on an infrequent basis, perhaps once or twice per year. Thus, the danger of catastrophic failure, including explosion, of very expensive transformers persists with the attendant loss of power distribution to critical processes such as chemical and semiconductor plants, or to businesses and consumers.

A common, known method of analyzing transformer oil for fault gas concentration involves obtaining a sample of the transformer oil, typically by extracting the oil with a syringe, and taking the oil to a laboratory for analysis by means such as gas chromatography.

It is common, for example, in using such methods to use vacuum extraction to extract the fault gases from the oil. As a result, heavy hydrocarbons can be extracted. Such heavy hydrocarbons can be separated from the more important lighter hydrocarbons via gas chromatography due to their longer retention times on columns. However, in order to use infra red (IR) sensing techniques it becomes necessary to remove these heavy hydrocarbons from the gas mixture. This separation can be accomplished by condensing the heavy hydrocarbons in a cold trap but this makes the process more expensive and may require the added maintenance of cooling systems and liquid disposal. While laboratory analysis is still the most common practice, there have been prior attempts to provide information in real-time using an on-line system. It should be noted that for such a device to be useful it must operate over a wide ambient temperature range (e.g. $-20°$ C. to $+50°$ C.), be able to handle varying oil temperatures (e.g. $0°$ C. to $+140°$ C.), and provide reliable data for many months without requiring service. To date, no such instrument has been realized.

Therefore, it is desirable to provide a sensor system capable of monitoring and measuring the concentration of fault gases in a liquid such as a transformer oil on a continuous, real-time basis using passive extraction techniques. It is desirable that such a system be capable of measuring the concentration of each of the fault gases of interest, and in the presence of other fault gases. It is further desirable that such a system be capable of unattended operation, requiring only periodic maintenance. It is also desirable that such a system be capable of: being remotely located with the transformer being monitored; sensing and determining the concentrations of fault gases present in the transformer oil; and transmitting resultant data to a central location for further analysis and follow-up action.

SUMMARY OF THE INVENTION

We have now discovered a method and apparatus for continuously monitoring and measuring the concentration of gases in a gas-containing liquid such as a transformer oil. The method and apparatus employ a passive gas extraction technique which comprises a high performance membrane material to extract dissolved gases from the oil, and an IR-based sensor to detect gases present. The method and apparatus is capable of measuring multiple gases of interest, simultaneously, without the need to separate the gases. The IR sensor comprises no moving parts. A thermal conductivity sensor measures the concentration of hydrogen, and the IR sensor measures the other gases of interest. The IR sensor comprises an internal reference which provides long term stability. Depending on the particular gas(es) present, the sensor is capable of a sensitivity of about 1–10 ppm. Because of the high sensitivity and quick response time of the invention, only a small portion of the dissolved gas need be extracted from the oil. Thus, the extracted gas is kept in a closed loop system and is maintained at equilibrium with the gas remaining dissolved in the oil, and is therefore completely non-consumptive and non-destructive of the gases. Therefore, unlike many of the previous approaches, the method and apparatus of the invention do not require the use of a carrier gas.

In a preferred aspect, this invention provides a sensor system for measuring the concentration of one or more constituent gases dissolved in a gas-containing liquid, the system comprising:

a. a passive gas extractor which extracts dissolved gas from the gas-containing liquid, there being a known relationship between the concentration of a constituent gas in the extracted gas and the concentration of the constituent gas remaining dissolved in the gas-containing liquid; and b. a gas sensor which senses the concentration of a constituent gas in the extracted gas, in the presence of other constituent gases, the gas sensor comprising
   (1) a sample chamber which receives the extracted gas,
   (2) a non-dispersive infrared (IR) absorption sensing system which generates an electrical signal corresponding to the light absorption, at one or more specified IR wavelengths, of the extracted gas in the chamber, and
   (3) an electrical output comprising the electrical signal generated by the non-dispersive IR absorption sensing system.

In a second preferred aspect, the invention provides a method of measuring the concentration of a gas dissolved in a gas-containing liquid, the gas comprising one or more constituent gases, the method comprising the steps of:

a. extracting a portion of the dissolved gas from the gas-containing liquid, there being a known relationship between the concentration of a constituent gas in the extracted gas and the concentration of the constituent gas remaining dissolved in the gas-containing liquid; and b. sensing the concentration of a constituent gas in the extracted gas, in the presence of other constituent gases in a gas sensor comprising:
   (1) a sample chamber which receives the extracted gas,
   (2) a non-dispersive infrared (IR) absorption sensing system which generates an electrical signal corresponding to the light absorption, at one or more specified IR wavelength, or the extracted gag in the chamber, and
   (3) an electrical output comprising the electrical signal generated by the non-dispersive IR absorption sensing system.

An apparatus for extracting dissolved gas from a gas-containing liquid and delivering the extracted gas to a collection station, suitable for use in the apparatus of this invention, is disclosed in copending, commonly assigned application the '942 patent. The apparatus extracts dissolved gas from the gas-containing liquid, and pumps the extracted gas to an external collector (e.g., the OBA described herein) where the extracted gas can be analyzed. In other applications, the gas can be separated into its various component gases and/or stored for later analysis. According to the invention disclosed in the '942 patent, there is provided an apparatus for extracting dissolved gas from a gas-containing liquid and delivering the extracted gas to a collection station, comprising:

a. a liquid pumping chamber having a wall formed of an elastic first diaphragm;

b. a reciprocable first actuator attached to the first diaphragm, the first actuator pressing the first diaphragm inwardly during its forward stroke and pulling the first diaphragm outwardly during its reverse stroke;

c. a separation cell partitioned into a feed chamber and a permeate chamber by a permselective membrane which, when a gas-containing liquid having at least one gas dissolved therein is introduced into the feed chamber, permits the at least one dissolved gas to diffuse thereacross and collect in the permeate chamber as extracted gas, but is substantially impermeable to the gas-containing liquid;

d. a first liquid conduit, for connecting the liquid pumping chamber to an external reservoir of the gas-containing liquid;

e. a second liquid conduit, for connecting the feed chamber to the external reservoir;

f. a liquid transfer conduit connecting the liquid pumping chamber and the feed chamber;

g. first and second check valves controlling the flow of the gas-containing liquid through the first liquid conduit and the liquid transfer conduit, respectively; one of the first and second check valves being oriented to permit flow of the gas-containing liquid into the liquid pumping chamber and the other of the first and second check valves being oriented to permit flow of the gas-containing liquid out of the liquid pumping chamber;

h. a gas pumping chamber having a wall formed of an elastic second diaphragm;

i. a reciprocable second actuator attached to the second diaphragm, the second actuator pressing the second diaphragm inwardly during its forward stroke and pulling the second diaphragm outwardly during its reverse stroke;

j. a first gas conduit, for connecting the gas pumping chamber to an external collection station for extracted gas;

k. a second gas conduit, for connecting the permeate chamber to the external collection station;

l. a gas transfer conduit connecting the gas pumping chamber and the permeate chamber;

m. third and fourth check-valves controlling the flow of extracted gas through the first gas conduit and the gas transfer conduit, respectively; one of the third and fourth check valves permitting flow of extracted gas into the gas pumping chamber and the other of the third and fourth check valves permitting flow of extracted gas out of the gas pumping chamber;

n. a lever-and-fulcrum combination wherein the lever is connected to the first and second reciprocable actuators such that rocking the lever causes a reciprocating action in the first and second actuators, with the first actuator being in its forward stroke when the second actuator is in its reverse stroke and vice-versa; and o. drive means for rocking the lever.

A method of extracting dissolved gas from a gas-containing liquid, suitable for use in the method and apparatus of this invention, is disclosed in the '676 application. According to the invention disclosed in Ser. No. 08/800,676, there is provided a method of extracting dissolved gas from a gas-containing liquid, comprising the steps of a. providing a separation cell having a permselective membrane comprising an amorphous perfluoro-2,2-dimethyl-1,3-dioxole polymer, the membrane partitioning the cell into a feed chamber and a permeate chamber;

b. introducing into the feed chamber a gas-containing liquid to which the membrane is substantially impermeable, the gas-containing liquid having at least one gas dissolved therein;

c. permitting the at least one gas to permeate across the membrane from the feed chamber to the permeate chamber; and d. removing the at least one gas from the permeate chamber.

In preferred embodiments the sensor system comprises a processor having an input coupled with the electrical output of the gas sensor. The processor receives the electrical signal corresponding to the light absorption, at the one or more specified IR wavelengths, of the extracted gas in the chamber, and therefrom computes the concentration of at least one gas constituent present in the extracted gas.

The IR sensor comprises broadband IR detectors and narrow band filters, the narrow band filters having a full width half maximum (FWHM) bandwidth of less than 0.5 $\mu$m. The narrow band filters may include filters having center wavelengths at one or more of the following wavelengths 2.59 $\mu$m, 3.32 $\mu$m, 4.25 $\mu$m, 4.67 $\mu$m, 7.65 $\mu$m, 10.6 $\mu$m, and 13.7 $\mu$m. The IR sensor has an optical path which is greater than 1 inch.

The use of a reference wavelength is an important improvement of this invention. Previous art has not included a useful means of reducing instrument drift. By monitoring certain reference wavelengths, system changes (e.g. changes in source intensity) can be measured and compensated. The IR detectors used to monitor reference wavelengths may include filters having center wavelengths at 3.91 $\mu$m and/or 9 $\mu$m.

The sensor system may include a thermal conductivity sensor to determine the concentration of hydrogen in the extracted gas. Such a thermal conductivity sensor may include a bridge circuit comprising negative temperature coefficient (NTC) thermistors. One NTC thermistor mounted so that its temperature is that of the extracted gas. A second NTC thermistor is mounted so that its temperature is that of the sensor environment. The output of the bridge circuit is a voltage which is proportional to the difference between the two temperatures. The thermal conductivity of the extracted gas is computed from this information, and the concentration of hydrogen in the extracted gas can be determined since the thermal conductivity of hydrogen is much greater than the thermal conductivity of the other extracted gases.

There are several advantages of the passive separation method described herein. Firstly, the distribution coefficient (Ostwald coefficient) of heavier hydrocarbons is very large (e.g. 11 for $C_3H_8$ versus 0.4 for $CH_4$) favoring high concentrations of gas in oil. Equivalent gas in oil concentrations of $CH_4$ and $C_3H_8$ would result in 25 times more $CH_4$ in the gas as compared to $C_3H_8$. There are several cases where the distribution coefficient favors the gas phase. For example, $H_2$, CO, and $CH_4$ all have distribution coefficients less than one which means that there will be more gas in the gas phase than exists in the oil phase. Measurement of the gas phase at equilibrium is easier than measuring gases extracted from an oil sample due to the higher concentrations.

BRIEF DESCRIPTION OF THE DRAWINGS

The invention is illustrated in the accompanying drawings, in which like components are given the same reference numerals in each FIG. in which they appear, and in which.

DETAILED DESCRIPTION OF THE INVENTION

Figure 1:
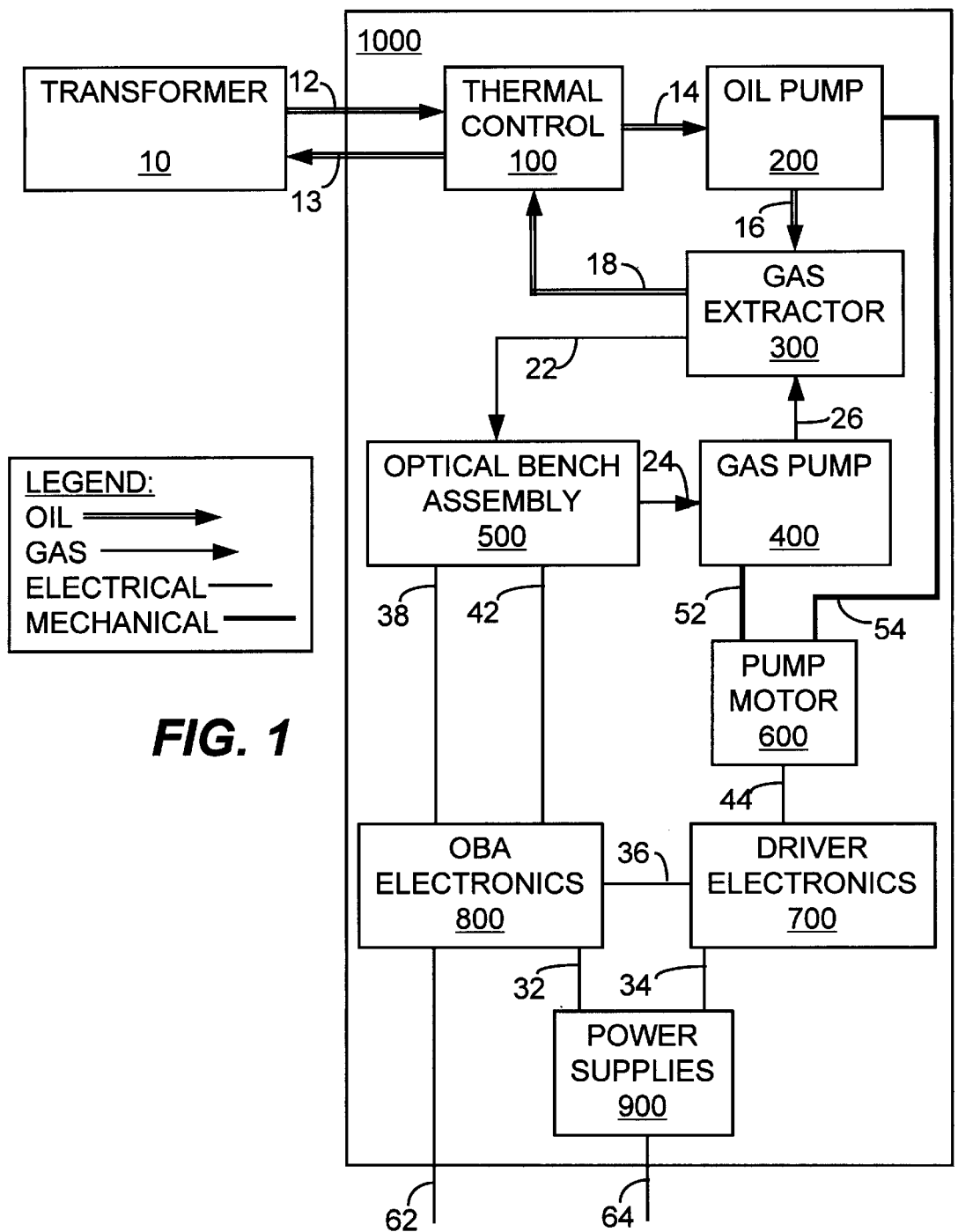
FIG. 1 is a functional block diagram which provides an overview of an embodiment of a gas sensor system of the invention.

FIG. 1 is a functional block diagram which provides an overview of an embodiment of a gas sensor system of the invention. The gas sensor system 1000 (the system) comprises a thermal controller 100, an oil pump 200, a gas extractor 300, a gas pump 400, an optical bench assembly (OBA) 500, a pump motor 600, driver electronics 700, OBA electronics 800 and power supplies 900. Oil received via a system input line 12 from an electrical transformer 10 is input to the system 1000 and passes through the thermal controller 100. The thermal controller 100 raises or lowers, as applicable, the temperature of the oil to 50° C.±2° C. Maintaining the temperature of the oil within this narrow temperature range facilitates determination of the concentrations of the constituent fault gases as only one value of the Ostwald coefficient (representing the relative apportionment of the gas between the oil and gas in equilibrium) need be used for each gas. In addition, the system environment is maintained at about 50° C., and it is advantageous to have the oil pass through the system at approximately the same temperature. However, in another embodiment, the thermal controller is not included, and the necessary calculations accommodate the added complexity.

The oil is output from the thermal controller 100 via an oil pump input line 14 and pumped by the oil pump 200 to the gas extractor 300 via an oil pump output line 16. After passing through the gas extractor 300, the oil returns via an output line 18 through the thermal controller 100 and then via a system output line 13 to the transformer 10.

The embodiment of the invention depicted in the FIGs. includes the oil pump 200. While the oil pump provides the advantage of guaranteeing a desired flow rate, and hence a guaranteed and short system response time (i.e. time to extract a sufficient gas sample and reach equilibrium), other embodiments do not include the oil pump. Instead the oil circulation is achieved by means of convection resulting from temperature differentials in the oil at the top and bottom of the electrical transformer or at the top and bottom of a mechanical system contained in the sensor system.

In the gas extractor 300, gases are extracted from the oil and, via the pumping action of the gas pump 400 pass via a gas line 22 to the OBA 500. From the OBA 500 gas returns via gas pump input line 24 and gas pump output line 26 to the gas extractor 300 via the gas pump 400. The extracted gas is in a closed loop comprising the gas extractor 300, OBA 500, gas pump 400 and respective gas lines 22 24 26. Once the extracted gas reaches equilibrium with the gas dissolved in the oil, the continued circulation of the extracted gas within this closed loop insures that the extracted gas remains in equilibrium with the gas dissolved in the oil. Another embodiment (not illustrated in the FIGs.) does not include the gas pump 400, but instead relies on diffusion of the extracted gas through the gas extractor 300 and OBA 500 loop by means of convection due to a temperature differential created in the OBA or in a separate gas mixing stage.

In the embodiment represented in FIG. 1, both the oil pump 200 and gas pump 400 are driven by a common pump motor 600. The pump motor actuates the oil pump 200 and gas pump 400 via mechanical linkage 52 54. In another embodiment of the invention (not illustrated in the FIGs.) the two pumps 200 400 are driven by their own respective motors. In still another embodiment of the invention (not illustrated in the FIGs.) the two pumps are driven by linear actuators, e.g. solenoids.

The OBA electronics 800 provides control and power signals via OBA control lines 42 to the OBA 500. The OBA 500 measures the absorption of light by the extracted gases and sends raw sensor signals via signal lines 38 to the OBA electronics 800. The OBA electronics 800 processes the received raw sensor signals and calculates the concentration of the extracted fault gases. Results calculated by the OBA electronics 800 are output to external systems (not illustrated in the FIGs.) via data lines 62. In another embodiment, the OBA electronics 800 simply converts the sensor signals to data quantities and transmits the data quantities to an external processor for calculation of the fault gas concentrations.

The driver electronics 700 provides control and power signals via motor control lines 44 to the pump motor 600. Input power is received by power supplies 900 via power lines 64. The power supplies 900 condition and convert the power to desired voltage levels and feed the power via power supply lines 32 34 to the OBA electronics 800 and driver electronics 700. Connection lines 36 between the driver electronics 700 and OBA electronics 800 facilitate distribution of one or more voltage levels received from the power supplies 900.

FIG. 1 provides a functional overview of an embodiment of a gas sensor system of the invention. The functions depicted in FIG. 1 are major functions performed by components of the gas sensor system 1000. Additional support functions, e.g. gas loop purge, are also performed by the various components, and will be described below in reference to subsequent FIGs. Also, as will be evident by the description of an embodiment of the invention herein, as well as references to other embodiments comprising alternate configurations, the functions depicted in FIG. 1 are not constrained to a one-to-one correspondence with individual components of a system of the invention. Rather, in embodiments of the invention, one or more functions may be performed by a single component, and/or one or more components may perform a single function.

Figure 2:
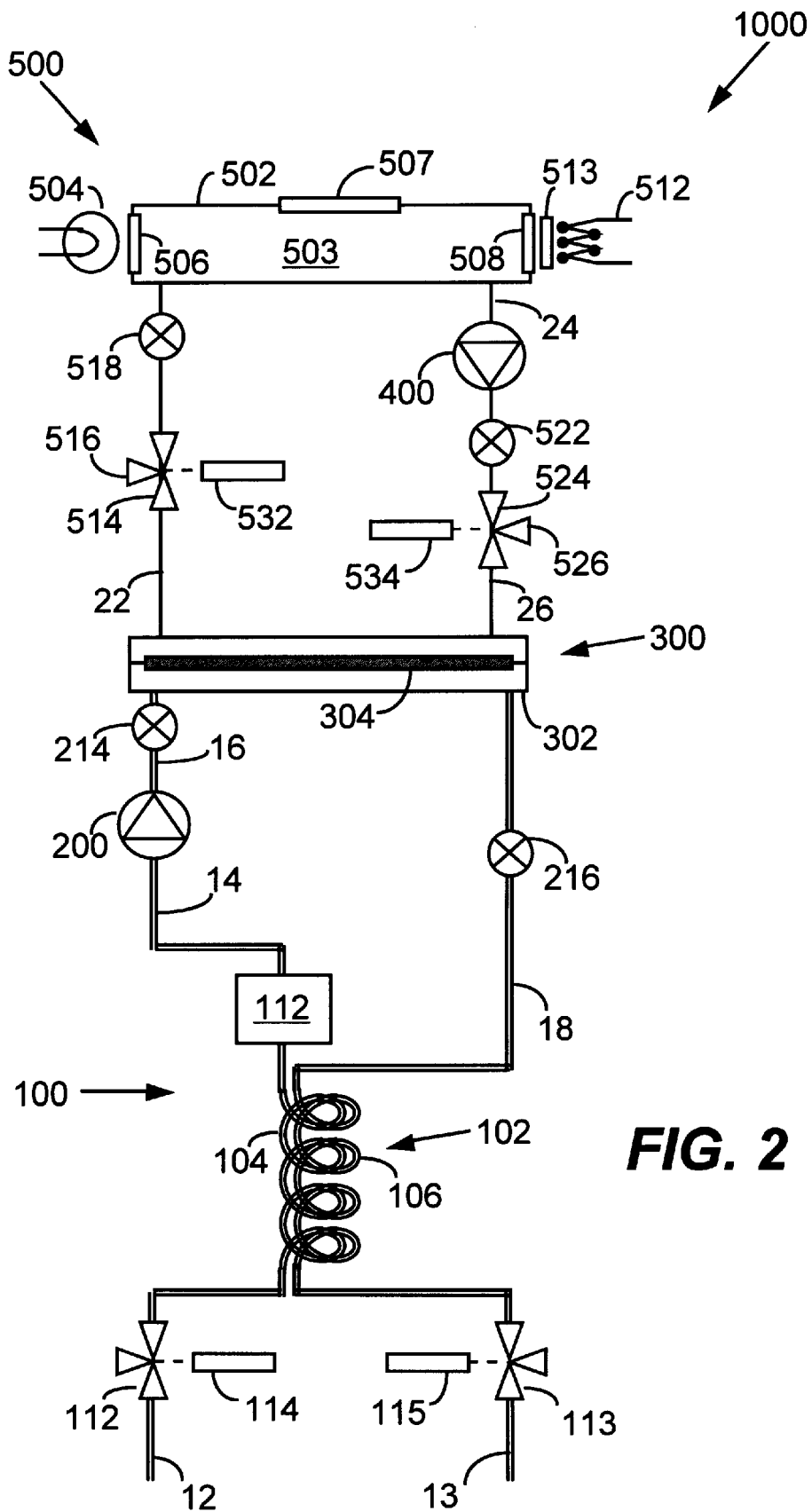
FIG. 2 is a mechanical schematic diagram of an embodiment of a gas sensor system of the invention.

FIG. 2 is a mechanical schematic diagram, not to scale, representative of an embodiment of a gas sensor system of the invention, and will be described to provide an overview of the mechanical features of the system. Major components of the system will be described in further detail following a description of FIG. 2. Oil enters the system 1000 via input line 12 under control of an input valve 112. The input valve 112 may be manually controlled or electrically actuated, for example by means of a solenoid 114. Oil flow through the system 1000 is facilitated by means of the oil pump 200. A first non-return check valve 214, coupled on the output side of the oil pump 200, and a second non-return check valve 216, coupled on the output side of the gas extractor 300, insure that oil flows only in the desired direction through the system 1000.

Upon entering the system 1000, the oil passes to a two-stage thermal controller 100 to bring the temperature of the oil to 50° C.±2° C. The first stage of the thermal controller 100 is a heat exchanger 102, which, in the embodiment depicted, comprises a tube-on-tube counter-flow arrangement. Oil entering the system 1000 passes through a first coil 104 and oil exiting the system 1000 passes, in a direction opposite that of the oil entering the system 1000, through a second coil 106. Oil entering the system 1000 can be at a higher or lower temperature than oil exiting the system 1000. As oil passes through the heat exchanger 102, the temperature of the oil entering the system 1000 is brought to within about 10° of 50° C. From the heat exchanger 102, the oil then moves to a thermoelectric device 112 which brings the temperature of the oil to 50°±2° C. The thermoelectric device 112 may be set-up to cool the oil or to heat the oil, as the case may warrant. A thermoelectric device suitable for use in the embodiment depicted by the mechanical schematic of FIG. 2 is a model CP1.4-127-06L manufactured by the Melcor Corporation.

From the thermoelectric device 112 the oil passes through the oil pump 200, and the first non-return oil check valve 214 to the gas extractor 300. In the gas extractor 300, dissolved gases separate from the oil and diffuse through a membrane 304. The oil then exits the gas extractor 300 and returns to the heat exchanger 102 via the second non-return oil check valve 216 and output line 18. The exiting oil passes through the second coil 106 and thence back to the transformer via the system output line 13. The oil exits the system 1000 under control of an output valve 113. The output valve 113 may be manually controlled or electrically actuated, for example by means of a solenoid 115.

Gas extracted from the oil exits the gas extractor 300 via a gas input line 22, through a first gas control valve 514, a first non-return gas check valve 518, and enters the OBA 500. The OBA comprises a sample chamber 502, typically in the form of one or more cylindrical tubes, one or more IR emitters 504, and one or more IR detectors 512. The IR emitters 504 and IR detectors 512 may be mounted at opposite ends of the sample chamber 502 as depicted in FIG. 2, or may be mounted at the same end with a reflector mounted at the opposite end (not illustrated in the FIGs.). The IR emitters 504 are separated from the interior 503 of the sample chamber 502 by a long-wave transmissive window 506, which may be comprised, for example, of silicon or germanium. The long-wave transmissive window 506 may have an anti-reflective coating to reduce losses due to reflection and thereby increase the transmissivity of the window 506. The IR detectors 512 are also separated from the interior 503 of the sample chamber 502 by a long-wave transmissive window 508. Each IR detector 512 comprises an IR filter 513 having a passband selected to facilitate identifying a gas of interest in the sample chamber 502. The IR emitters 504 may comprise any suitable IR light source, e.g., incandescent bulbs. The IR detectors 512 may comprise any suitable IR detector, e.g., pyroelectric detectors, thermopiles and Golay detectors.

In addition to the IR emitters 504 and detectors 512, the OBA also includes a thermal conductivity sensor 507 mounted to a wall of the sample chamber 502.

The first gas control valve 514 and second gas control valve 522 can be used to facilitate purging the system 1000 of any residual fault gases. A source of nitrogen (not depicted in FIG. 2) may be connected to a normally closed input 516 of the first gas control valve 514, and a normally closed output 526 of the second gas control valve 524 may be connected to an external purge line (not depicted in FIG.

2). The first and second gas control valves 514 524 may be operated manually or electrically actuated, for example, by means of first and second solenoids 532 534.

Gas leaves the sample chamber 502 via a gas output line 24 and is pumped by the gas pump 400 through a second non-return gas check valve 522 and a second gas control valve 524, and reenters the gas extractor 300. In order to maintain the extracted gas at equilibrium with the gas dissolved in the oil, some of the gas in the gas extractor may pass through the membrane 304 and diffuse back into the oil.

Figure 3:
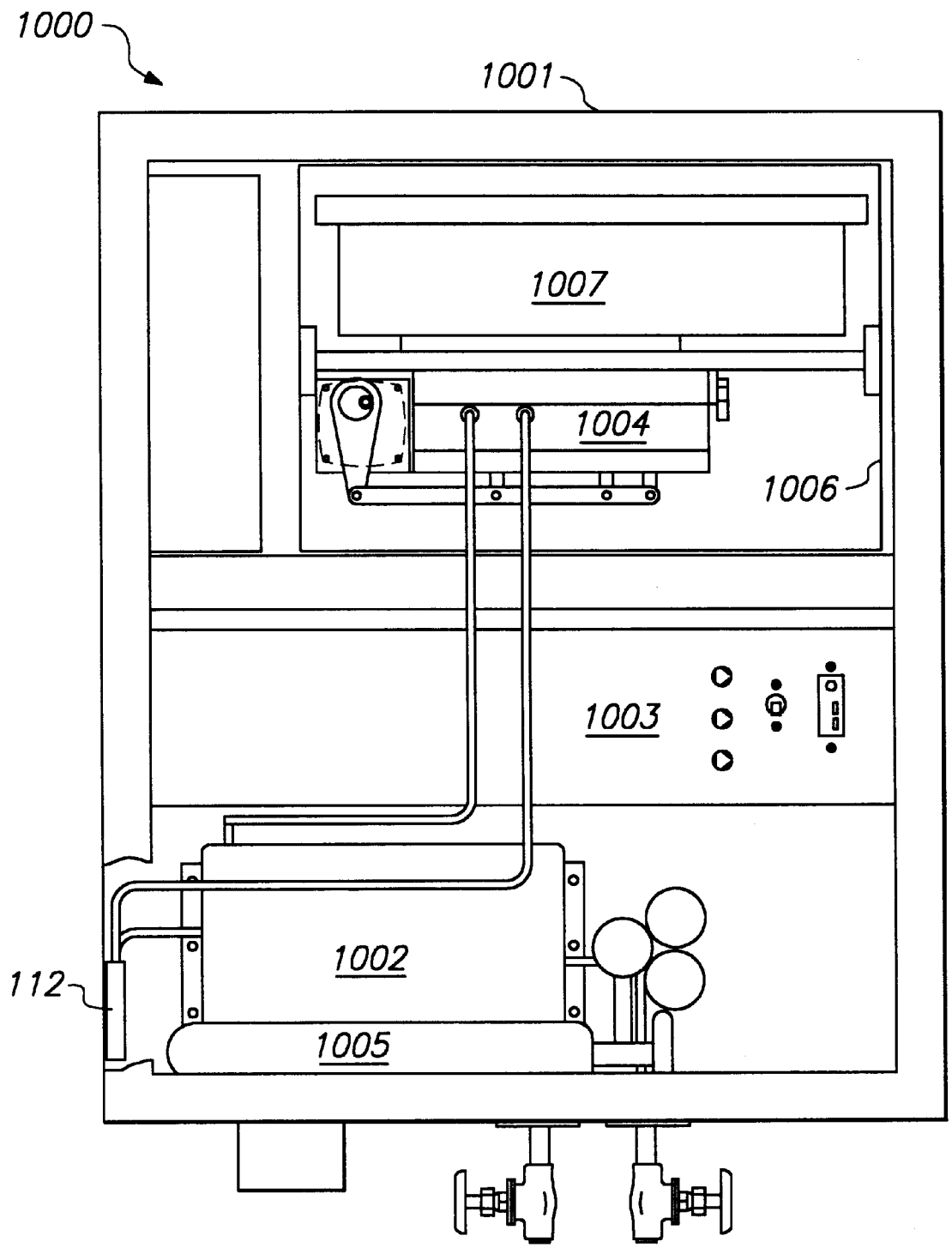
FIG. 3 is an external assembly view of an embodiment of a gas sensor system of the invention.

FIG. 3 is an external assembly view of an embodiment of a gas sensor system 1000 of the invention. The equipment is housed in a standard NEMA approved cabinet 1001 as can be purchased from Hoffman Co.. The equipment comprises a heat exchanger box 1002 which houses the heat exchanger 102; the thermoelectric device 112; an electrical cabinet 1003 which houses the driver electronics 700, OBA electronics 800 and power supplies 900; an integrated pump-extractor 1004 which comprises the pump motor 600, gas pump 400, gas extractor 300 and gas pump 400; and an OBA cabinet 1007 which houses the OBA 500. Also included is a gas cylinder 1005 which contains nitrogen for purging the OBA 500. The integrated pump extractor 1004 and OBA cabinet 1007 are housed in a temperature controlled region 1006. This region is controlled to within ±5° C. Additionally, the OBA 500 is housed in the OBA cabinet 1007, and the temperature of the environment within the OBA cabinet 1007 is controlled to within ±0.5° C. Careful attention to temperature control with the possibility of multiple temperature controlled regions is an important advancement of this invention.

Figure 4:
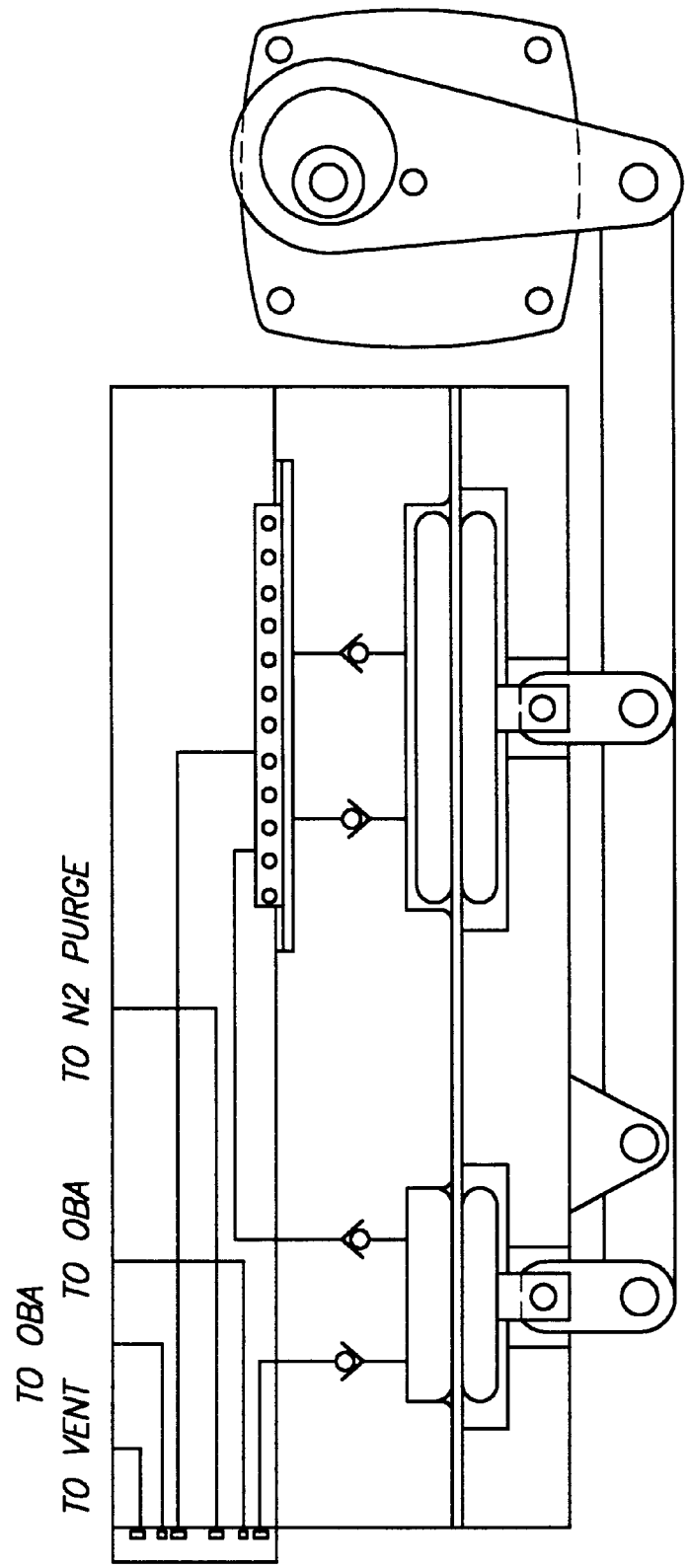
FIG. 4 is an external view of an embodiment of an apparatus comprising an oil pump, a gas extractor, a gas pump, and a pump motor suitable for use in an embodiment of a gas sensor system of the invention.

FIG. 4 is an external view of an embodiment of an apparatus comprising an oil pump 200, a gas extractor 300, a gas pump 400, and a pump motor 600 suitable for use in the gas sensor system 1000 of the invention. FIG. 4 is the same as the FIG. 1 in the '942 patent. The description of FIG. 1 of the '942 patent is incorporated herein, in its entirety, by reference.

Figure 5:
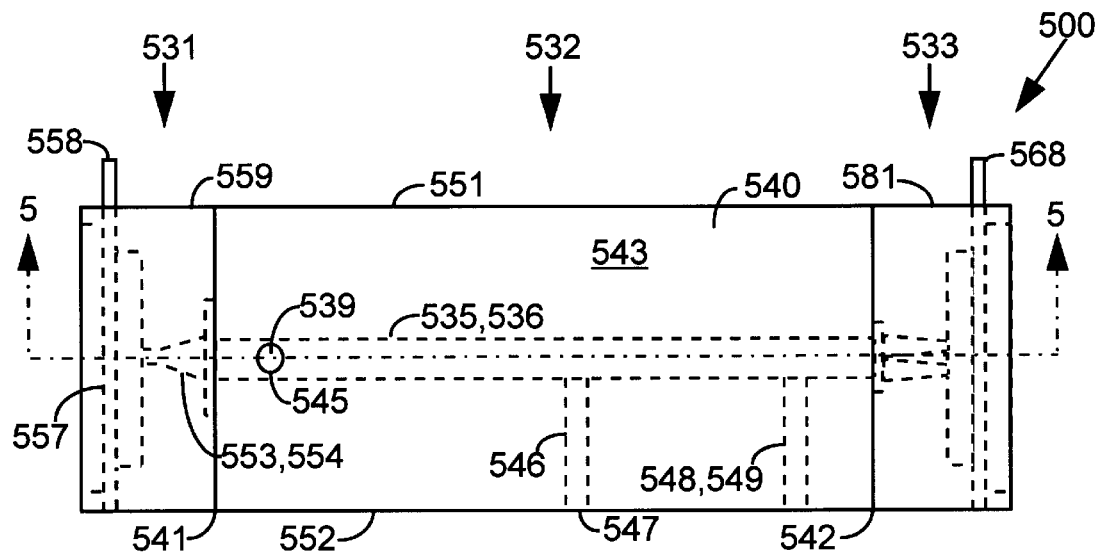
FIG. 5 is an external view of an embodiment of an OBA suitable for use in an embodiment of a gas sensor system of the invention.
Figure 6:
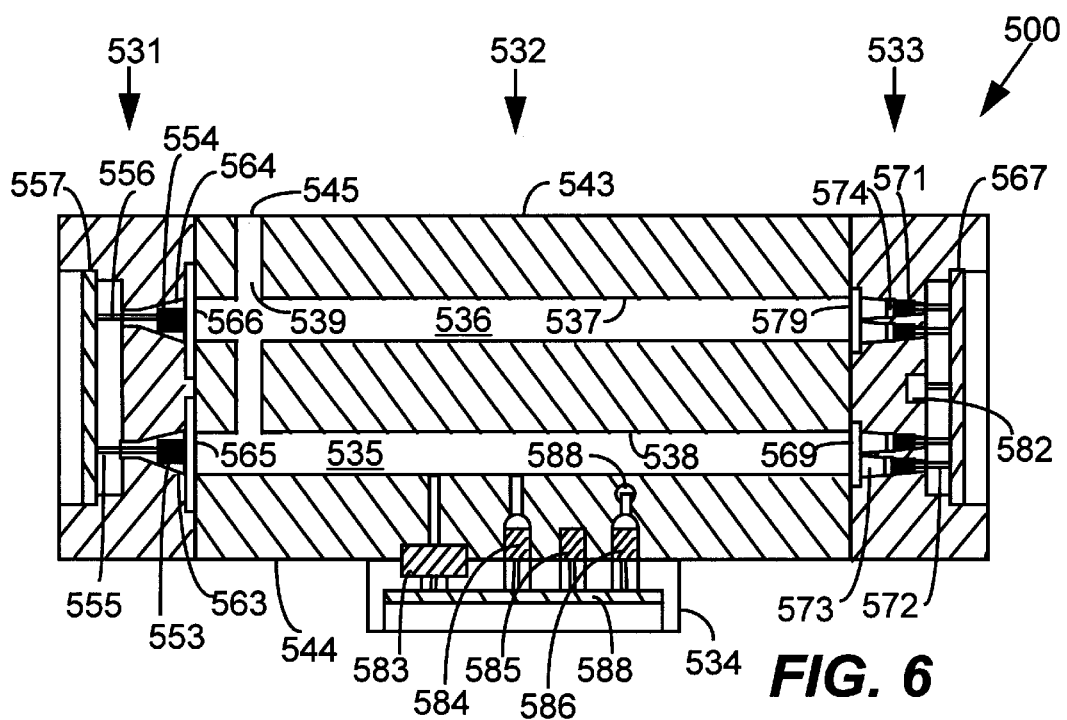
FIG. 6 is a cross sectional view of the embodiment of an OBA in FIG. 5, taken at the plane 5—5 of FIG. 5.

FIG. 5 is an external view of an embodiment of an OBA 500 suitable for use in the apparatus of the invention. FIG. 6 is a cross sectional view of the embodiment of an OBA 500 in FIG. 5, taken at the plane 5—5 of FIG. 5. The OBA will be described with reference to both FIGS. 5 and 6. Mounting hardware, such as screws, nuts, bolts, etc. is not depicted in the FIGs.

The OBA 500 comprises several sections, including an emitter section 531, a sample section 532, a detector section 533, and thermal conductivity section 534. In the embodiment shown, the sample section 532 comprises a substantially rectangular block 540 having a length defined by a first end 541 and a second end 542. For purposes of this description, the sample section 532 may also be considered as having a first side 543, a second side 544, a top 551, and a bottom 552. While the description of the embodiment represented in FIGS. 5 and 6 refers to various features in terms of their respective relationships with the several faces (i.e., sides, top, bottom), it is understood that the invention is not so restricted, and the details of the configuration may vary according to design choice.

First and second longitudinal cylindrical tubes 535 536 (represented by the sample chamber 502 in FIG. 2) extend the length of the sample section 532. The longitudinal tubes 535 536 have inner walls 537 538 which are polished smooth to provide a specular reflecting surface. While the embodiment shown comprises two longitudinal cylindrical tubes 535 536, other embodiments may comprise only one such tube, or more than two such tubes. Located proximate one end of the tubes 535 536 is a transverse tube 539 which couples the two longitudinal cylindrical tubes 535 536, and has an exit 545 at the first side 543 of the sample section 532. During normal operation, the transverse tube 539 is plugged (not illustrated in the FIGs.) at the exit 545. A purge tube 546 has an entrance 547 at the bottom 544 of the sample section 532, and couples to a longitudinal tube 536. During normal operation, the purge tube 546 is plugged (not illustrated in the FIGs.) at the entrance 547. The OBA 500 can be purged of extracted gases by removing the plugs from both the purge tube 546 and the transverse tube 539, and flowing nitrogen through the assembly. An extracted gas inlet tube 548 and an extracted gas outlet tube 549, enter and exit, respectively, the bottom 552. The extracted gas inlet tube 548 couples with one of the longitudinal tubes 535 and the extracted gas outlet tube 549 couples with the other of the longitudinal tubes 536 thereby setting up a closed path (including the transverse tube 539) by which extracted gases flow within the sample section 532 of the OBA 500.

The emitter section 531 is mounted to and mated with the first end 541 of the sample section 532. The emitter section 531 includes first and second IR emitters 553 554. The IR emitters 553 554 comprise leads 555 556 which are mounted to an emitter circuit board 557. The emitter circuit board 557 is housed within the emitter section 531 and has an emitter circuit board extension 558 which extends outside a top face 559 of the emitter section 531. The emitter circuit board extension 558 may plug into an electrical connector (not illustrated in the FIGs.) or otherwise facilitate coupling the emitter circuit board 557 with the OBA electronics 800.

In the embodiment depicted in FIGS. 5 and 6, the IR emitters 553 554 are mounted within conical apertures 563 564 formed in the emitter section 531. The conical apertures 563 564 are elliptical in cross section (not illustrated in the FIGs.) and serve as reflectors to bounce the energy from the IR emitters 553 554 off the walls of the longitudinal cylindrical tubes 535 536 in order to obtain a longer path length. In this embodiment of a gas sensor system 1000 of the invention, one IR emitter 553 is an incandescent bulb having a tungsten filament and rated at about one-half watt. Such a bulb can be purchased from Carley Lamp. The second emitter 554 is an incandescent bulb having a platinum-iridium filament. The bulbs are selected to provide energy in the wavelengths corresponding to the fault gases of interest.

The IR emitters 553 554 are separated from the longitudinal tubes 535 536 by emitter long-wave transmissive windows 565 566. A first emitter long-wave transmissive window 565, used in conjunction with the tungsten bulb IR emitter 553, is a cut-on filter that passes light in a band which includes the shorter wavelengths of interest, e.g. about 2.5 to 4.7 $\mu$m. A second emitter long-wave transmissive window 566, used in conjunction with the platinum-iridium bulb IR emitter 554, is a wide pass filter, and passes light in the longer wavelengths of interest, e.g. about 7.5 to 15 $\mu$m. Such long-wave transmissive windows are available from the Optical Coating Laboratory, Inc. (OCLI).

The detector section 533 is mounted to and mated with the second end 542 of the sample section 532. The detector section 533 includes eight IR detectors 571 (only 4 are visible in FIG. 6). Each IR detector 571 comprises leads 572 which are mounted to a detector circuit board 567. The detector circuit board 567 is housed within the detector section 533 and has a detector circuit board extension 568 which extends outside a top face 581 of the detector section 533. The detector circuit board extension 568 may plug into an electrical connector (not illustrated in the FIGs.) or otherwise facilitate coupling the detector circuit board 567 with the OBA electronics 800.

In the embodiment depicted in FIGS. 5 and 6, the IR detectors 571 are mounted within eight conical apertures 573 (only 4 are visible in FIG. 6) formed in the emitter section 531. The conical apertures 573 are circular in cross section (not illustrated in the FIGs.) and serve as reflectors to direct IR energy to the IR detectors 571. The IR detectors 571 are separated from the interior of the longitudinal tubes 535 536 by detector long-wave transmissive windows 569 579. The detector long-wave transmissive windows 569 579 are typically the same as the respective corresponding emitter long-wave transmissive windows 565 566., i.e. a first detector long-wave transmissive window 569 that passes light in a band which includes the shorter wavelengths of interest, e.g. about 2.5 to 4.7 $\mu$m, and a second emitter long-wave transmissive window 579 that passes light in the longer wavelengths of interest, e.g. about 7.5 to 15 $\mu$m. In another embodiment of the invention, the windows are broadband windows transmissive over a wider wavelength region (e.g. 2–15 $\mu$m).

In the embodiment depicted in FIGS. 5 and 6, the OBA 500 comprises eight IR detectors 571. The eight IR detectors 571 are substantially identical, however, each IR detector also comprises a narrowband IR filter 574, with each IR filter 574 centered at a wavelength of interest. IR detectors which may be used in the invention include pyroelectric detectors, thermopiles, Golay detectors and the like. ELTEC 481 pyroelectric detectors are used in one embodiment of the invention. Table 1 lists center wavelengths for candidate filters, and the purpose of each filter. The IR filters 574, available from OCLI, have a full width half maximum (FWHM) bandwidth of less than 0.5 $\mu$m. Nine such candidate center wavelengths are listed in Table 1, with eight selected for use in the embodiment of the invention described herein.

TABLE 1

| Wavelength | IR Filters Purpose |
|---|---|
| 2.59 $\mu$m | Detect water ($H_2O$) |
| 3.32 $\mu$m | Detect ethane ($C_2H_6$) |
| 3.91 $\mu$m | Zero equipment |
| 4.25 $\mu$m | Detect carbon dioxide ($CO_2$) |
| 4.67 $\mu$m | Detect carbon monoxide (CO) |
| 7.65 $\mu$m | Detect methane ($CH_4$) |
| 9 $\mu$m | Zero equipment |
| 10.6 $\mu$m | Detect ethylene ($C_2H_4$) |
| 13.7 $\mu$m | Detect acetylene ($C_2H_2$) |

The eight IR detectors 571 are arranged in two groups of four detectors each, with each group of detectors positioned to receive IR energy from one of the two IR emitters 553 554 via a corresponding longitudinal cylindrical tube 535 536. Within each group of four IR detectors 571, three IR detectors 571 have IR filters 574 selected to detect one of the fault gases of interest. The fourth IR filter 574 is selected to have a passband at a wavelength which is unaffected by fault gases which may be present, and therefore is used to calibrate and zero the sensor system 1000. Also mounted in the detector section 533 is a detector section temperature sensor 582.

The use of a reference wavelength is an important improvement of this system. Previous art has not included a useful means of reducing instrument drift. By monitoring the reference wavelengths, system changes (e.g. changes in source intensity) can be measured and compensated. In particular, the actual absorption can be corrected for drift using the formula:

Actual Change=(Counts−Counts$_0$)/Counts$_0$+k$_{ref}$(Reference counts−Reference counts$_0$)/Reference counts$_0$ where the constant $k_{ref}$ can be determined experimentally (e.g. by dimming the source) or via experience. This internal reference combined with the possible addition of rezeroing using a nitrogen source provides long term stability required in this application.

The thermal conductivity section comprises a pressure sensor 583, a first NTC thermistor 584, a thermal conductivity section temperature sensor 585, and a second NTC thermistor 586. The pressure sensor 583 senses the pressure of the extracted gas in the longitudinal cylindrical tubes 535 536. The thermal conductivity section temperature sensor 585 senses the temperature of the assembly in the environment of the thermal conductivity section. The first NTC thermistor 584 is responsive to the temperature of the extracted gas in the longitudinal cylindrical tubes 535 536. The second NTC thermistor 586 is responsive to the temperature of the nitrogen gas in a reference section tube 587 in the sample section 532. The first NTC thermistor 584 and second NTC thermistor 586 are held in a bridge circuit (not illustrated in the FIGs.). The bridge circuit generates a voltage proportional to the temperature of the first NTC thermistor 584 and hence the temperature of the extracted gas. It is known to measure the thermal conductivity of the extracted gas in this manner, and hence to measure the concentration of the hydrogen since the thermal conductivity of hydrogen is much greater than that of other constituent gases in the extracted gas. The four sensors 583 584 585 586 are mounted to a thermal conductivity circuit board 588, and the respective electrical signals are coupled to the OBA electronics 500. The pressure and temperature values are used in the computation of the concentrations of constituent fault gases in the extracted gas.

Figure 7:
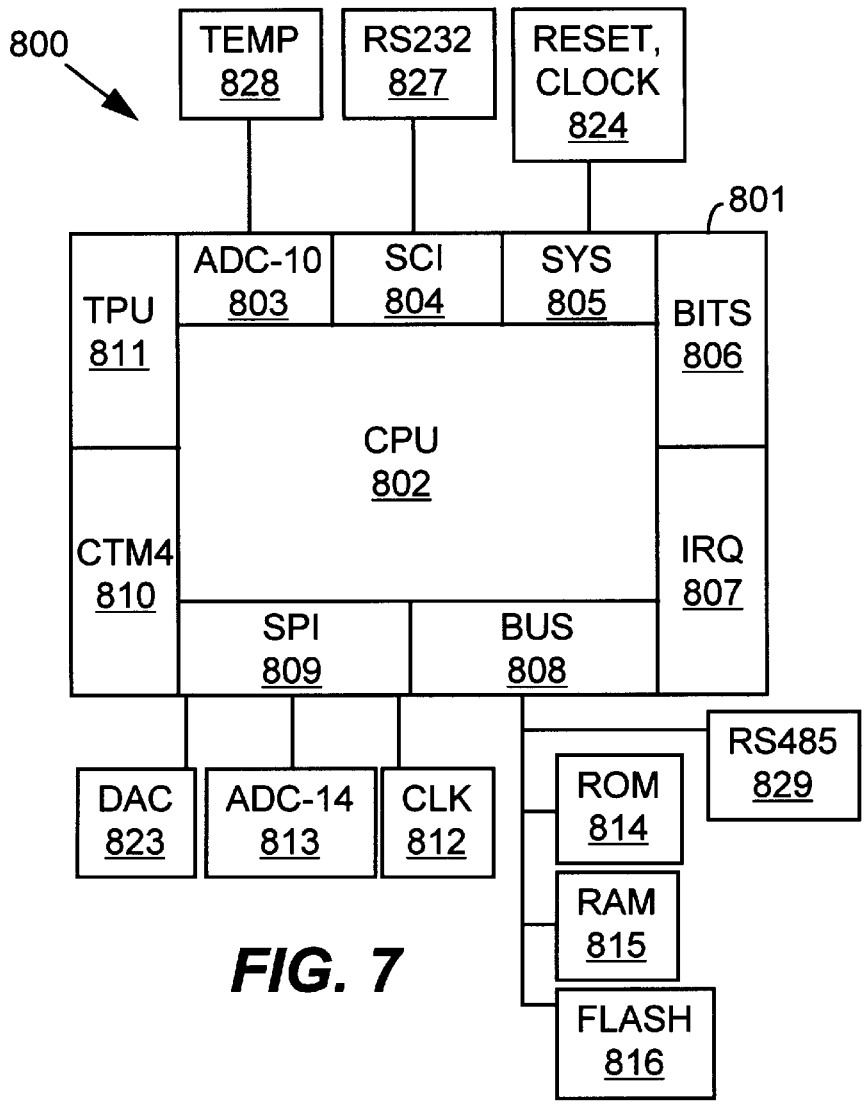
FIG. 7 is diagram of an embodiment of an OBA electronics suitable for use in a gas sensor system of the invention.

FIG. 7 is a diagram of an embodiment of an OBA electronics 800 suitable for use in a gas sensor system of the invention. The OBA electronics 800 comprises a microcontroller 801 and signal conditioning circuitry to control lamps, heaters and valves, measure lamp intensity, temperature and pressure, and interfaces to communicate with other computers and the like. In one embodiment, the microcontroller 801 is a Motorola MC68336ACFT16 processor. However, other equivalent commercially available processors may be used. The microcontroller 801 comprises a central processing unit (CPU) 802, a ten bit analog to digital converter (ADC-10) 803, a serial communication interface (SCI) 804, a system reset and clock input (SYS) line 805, a discrete section (BITS) 806, an interrupt request line (IRQ) 807, a bus and chip select (BUS) section 808, a system parallel interface (SPI) 809, a configurable timer module (CTM) section 810, and a time processor unit (TPU) 811.

The microcontroller 801 receives temperature and pressure data from the respective sensors via temperature and pressure drivers 828 coupled with the ADC-10 803. The SCI 804 is coupled with an RS232 driver 827, and communicates with external computers (not illustrated in the FIGs.). The discrete section (BITS) 806 controls valves, lamps, a cooling fan (not illustrated in the FIGs.) and the like via discrete drivers 825. The IRQ 807 is coupled with an RS485 bus port 826. The BUS 808 couples the microcontroller to a read only memory (ROM) 814, a random access memory (RAM) 815, a flash memory (FLASH) 816, and an RS485 bus driver 829. The SPI 809 couples the microcontroller with a 12 bit digital to analog converter (DAC) 823, a real time clock 812, and a 14 bit analog to digital converter (ADC-14) 813. The microcontroller 801 controls the thermoelectric device 112 (FIG. 2), the IR emitters 553 554 (FIG. 6) and heaters which control the temperature of the equipment (not illustrated in the FIGs.) via the DAC 823. The TPU 811 interfaces with the IR detectors 571 to accumulate clock counts as described below in reference to FIG. 8. The CTM 810 interfaces with a series of drivers 831 which interface with the various system environment heaters (not illustrated in the FIGs.). The IRQ 807 receives interrupt requests from the RS485 bus 826 and the ADC-14 813. The operation of the system software resident in the CPU 802 will be discussed below with reference to FIG. 9.

Figure 8:
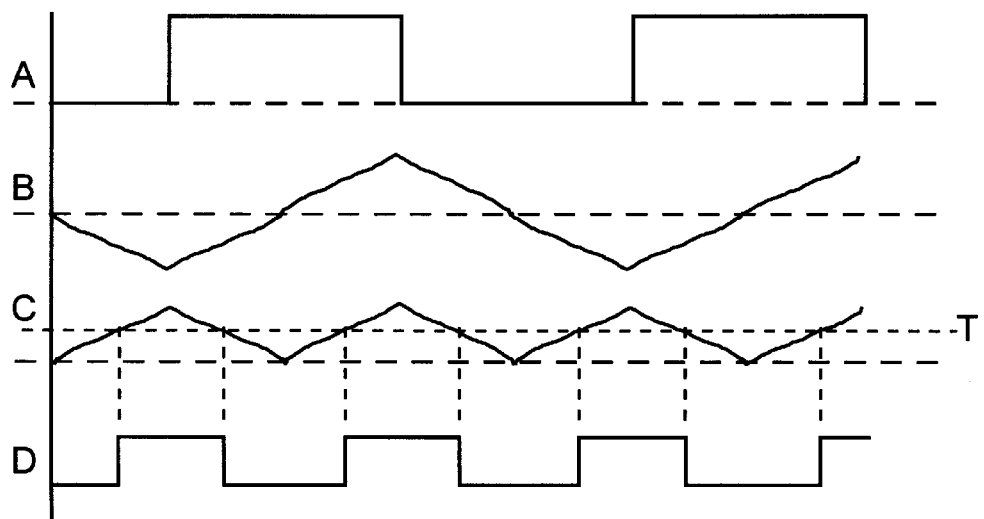
FIG. 8 is a graphical plot which represents a method by which the concentration of fault gases is sensed in an embodiment of a gas sensor system of the invention.

FIG. 8 is a graphical plot representing a method by which the concentration of fault gases is sensed in an embodiment of a gas sensor system 1000 of the invention. The waveforms plotted in FIG. 8 are meant to be merely illustrative of the approach, and are not plotted to scale. Referring back to FIGS. 6, extracted fault gases are detected by means of the IR emitters 553 554 emitting light in the range of about 2.5 to 15 μm, and the IR detectors 571 detecting the light energy which passes through the extracted fault gases contained in the longitudinal cylindrical tubes 535 536. Associated with each IR detector 571 is a narrow bandpass filter 574 having a center wavelength selected to correspond with an absorption wavelength of a particular fault gas of interest. Waveform A represents the output of one of the IR emitters 553 554 which has a one second duty cycle (i.e. ON for one second and OFF for one second). The one second duty cycle is controlled electronically by the OBA electronics 800 and requires no moving parts. Waveform B represents the response of one of the IR detectors 571, at the output of a preamp (not illustrated) on the detector circuit board 567. The output of the preamp is periodic and tracks the square wave representing the IR emitter 553 554 output. Waveform C represents the response after it has been further amplified and rectified. Associated with waveform C is a threshold level T. The period of time during the ON half of the duty cycle in which waveform C is above threshold T is a function of the concentration of the particular fault gas. Waveform D represents the time periods during which the level of waveform C exceeds threshold T. A clock/counter (not illustrated in the FIGs.) is sampled during these periods with the count accumulated during each such period passed to the microcontroller 801 for processing. In one embodiment of a sensor system of the invention, the clock/counter is run at a clock rate sufficient to provide timing information to 18 bit accuracy, resulting in a concentration computation accuracy of between 1–10 ppm.

Figure 9:
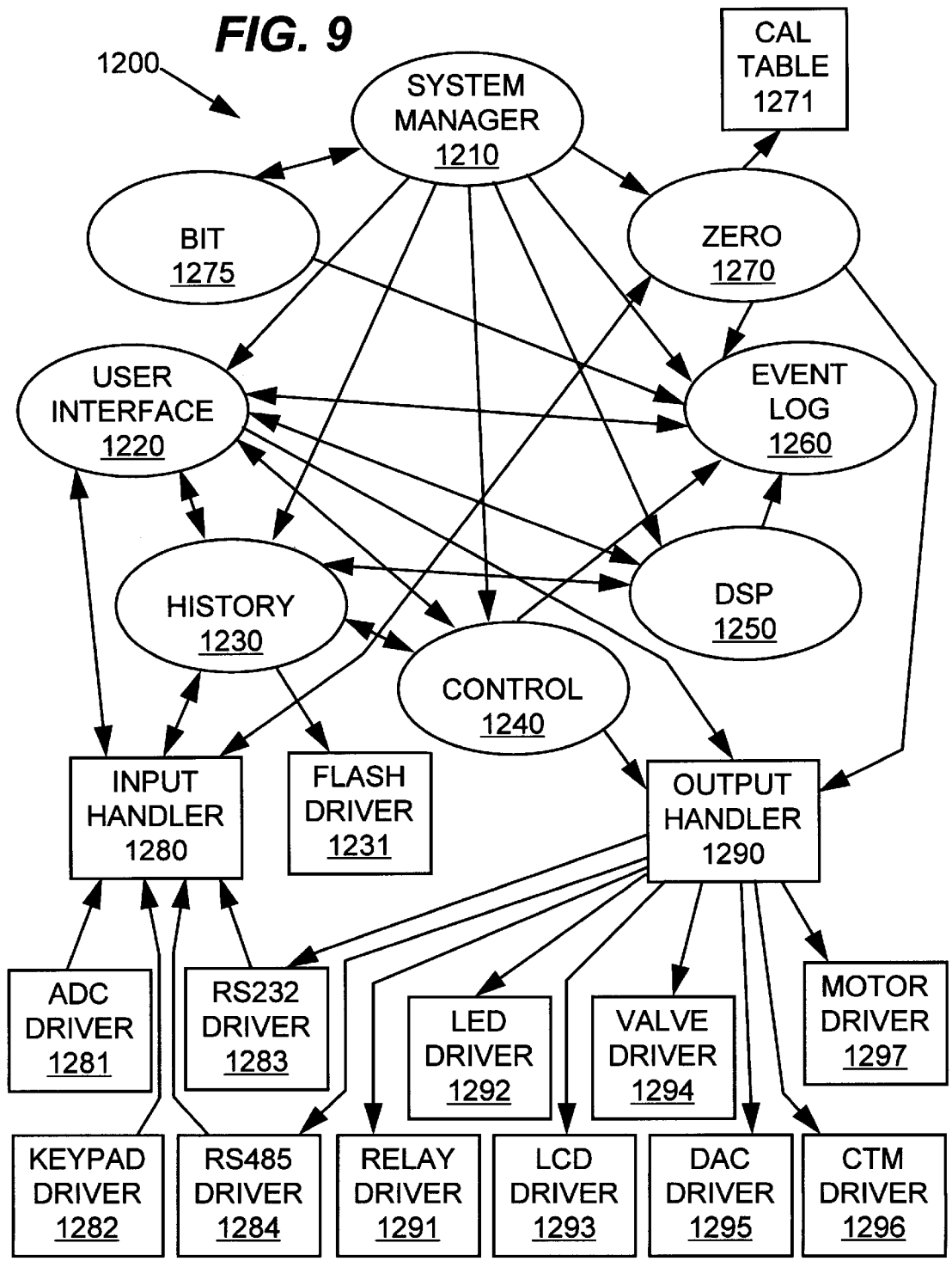
FIG. 9 is a diagram of a software architecture suitable for use in a gas sensor system of the invention.

FIG. 9 is a diagram which depicts the architecture of the system software 1200 which runs in the microcontroller 801 CPU 802 in one embodiment of a gas sensor system 1000 of the invention. The system software comprises a system manager 1210, a user interface process 1220, a history process 1230, a control process 1240, a digital signal processing (DSP) process 1250, an event log process 1260, a zero process 1270 and a built in test (BIT) process 1275.

The system manager 1210 exercises overall control over the system software 1200. The system manager 1210 is responsible for starting the various processes and for their proper sequencing.

The user interface process 1220 provides the input and output functions necessary for an operator to set up and run the system 1000. The user interface process 1220 also provides the necessary interface to permit the system 1000 to run unattended and communicate with a remote operator or remote computer system(s) (not illustrated in the FIGs.). The user interface process 1200 also provides the necessary interface to support system development, debugging, service and other utility functions. The user interface process 1220 is supported by an input handler 1280 and an output handler 1290 which in turn are supported by several input and output device drivers. Input device drivers which support the user interface process 1220 include an RS232 driver 1283, a keypad driver 1282 and an RS485 driver 1284. Output device drivers which support the user interface process 1220 include a light emitting diode (LED) driver 1292, a liquid crystal display (LCD) driver 1293, the RS232 driver 1283 and the RS485 driver 1284. Other embodiments may include other drivers to support communications with additional media, such as ethernet, wireless, etc.

The RS232 driver 1283 supports connecting a processor such as a Personal Computer (PC) (not illustrated in the FIGs.) to the System 1000 for development, debugging, field service and the like. The RS485 driver 1284 permits the system 1000 to be connected to an RS485 bus (not illustrated in the FIGs.) for communication with a distant operator, for example in a central location. The RS485 driver 1283 also permits the system 1000 to be connected with other systems on an RS485 bus (not illustrated in the FIGs.), with all systems communicating back to an operator at a central location. A keypad driver 1282 supports a keypad (not illustrated in the FIGs.) which may be attached to the system 1000 temporarily or permanently to support an operator performing system checkout, field service and the like.

Both the RS232 driver 1283 and the RS485 driver 1284 also support the output function of the user interface process 1220 via the output handler 1290. In operation, in response to incoming requests, the user interface process 1220 sends data requests to the history process 1230, control process 1240, DSP process 1250 and event log process 1260. The requested data is sent back to the user interface 1220 process by the process receiving the request. The user interface process 1220 may also send subscription requests to the input handler 1280 requesting that certain incoming data be supplied to the user interface process 1220 on an as received or periodic basis.

The input handler 1280 receives the incoming temperature, pressure and concentration data. Temperature and pressure data is received via an analog to digital converter (ADC) driver 1281. The input handler 1280 receives and stores the raw temperature and pressure data. The input handler 1280 also filters the incoming data, computing, for example, average values over a 1 minute period. Both the raw and average values are stored by the input handler 1280 and provided, as requested, to the history process 1230. The input handler 1280 also receives, stores, filters and forwards raw gas concentration measurements from an input capture timer, such as may be part of a time processor unit (TPU) 811 incorporated within the microcontroller 801 (FIG. 7).

The history process 1230 process also receives a variety of data from other processes, and stores the data with a time stamp, via a flash memory driver 1231 in a non-volatile flash memory 815 (FIG. 7). The history process 1230 may also request and receive sensor data and control data from the control process 1240 and DSP process 1250. The history process 1230 process may subscribe to receive the data on a periodic basis, on an exception basis (e.g. only in case of a change which exceeds a threshold), or on both a periodic and exception basis.

The control process 1240 is responsible for maintaining the temperature of the system environment and the sample oil. The control process 1240 receives the temperature and pressure data from the history process 1230, and adjusts heaters (not illustrated in the FIGs.) positioned within the system environment as appropriate. Voltage corrections are sent to the heaters via a digital to analog converter (DAC) driver 1295. The control process 1240 also controls the pump motor 600 via a motor driver 1297. A CTM driver 1296 provides pulse width modulation of the power for some heaters.

The DSP process 1250 converts measured gas concentration from counts to parts per million, incorporating various correction factors for lamp intensity, sensor temperature, oil pressure, vapor temperature, etc.

Several processes, including the control process 1240, DSP process 1250, user interface process 1220 and input handler 1280 detect discrete events, such as alarms, status changes, etc., and report these discrete events to the event log process 1260. The event log process 1260 stores the event data with a time stamp.

The zero process 1270 causes nitrogen to be introduced to the OBA 500 by switching the first and second gas control valves 514 524 (FIG. 2) After a period of time sufficient for the OBA 500 to be swept free of extracted gases or other vapors present, the zero gas concentration is measured and stored in a calibration table 1271.

The BIT process 1275 examines the OBA electronics 800 periodically to assure the components are working properly. Any faults are reported to the system manager 1210 and the event log 1260 process.

What is claimed is:

1. A sensor system for measuring the concentration of gas dissolved in a liquid, the gas comprising one or more constituent gases in a distribution, the system comprising:
   a. a passive extractor which extracts dissolved gas from the gas-containing liquid, there being a known relationship between the concentration of a constituent gas in the extracted gas and the concentration of the constituent gas remaining dissolved in the gas-containing liquid; and
   b. a gas sensor which senses the concentration of a constituent gas in the extracted gas, in the presence of other constituent gases, the gas sensor comprising
      (1) a sample chamber having plural tubes which receive the extracted gas,
      (2) a non-dispersive infrared (IR) absorption sensing system which generates an electrical signal corresponding to the light absorption, at one or more specified IR wavelengths, of the extracted gas in the chamber, and
      (3) an electrical output comprising the electrical signal generated by the non-dispersive IR absorption sensing system comprising a respective IR emitter disposed at one end of a respective tube, each IR emitter comprising a blackbody source for emitting IR light with wavelengths in the range 2.5 to 15 $\mu$m, a filter for limiting the IR light transmitted in each tube to a respective sub-range of wavelengths, and plural IR detectors disposed at an opposite end of each of said tubes for receiving the light transmitted in said tube to produce an electrical output signal as a function of the intensity of the received light, each IR detector being tuned to a predetermined wavelength in said respective sub-range corresponding to a respective one of said constituent gases to produce a detection signal representing the presence of said one constituent gas if IR light at said predetermined wavelength is of reduced intensity.

2. The sensor system according to claim 1 comprising a compressor receiving the detection signals produced by said IR detectors, and therefrom computing the concentration of at least one constituent gas present in the extracted gas.

3. The system according to claim 1 comprising:
   a. means for receiving a gas-containing liquid from a liquid reservoir; and
   b. means for returning liquid to the liquid reservoir.

4. The system according to claim 1 comprising:
   a. means for passing extracted gas to the gas sensor; and
   b. means for returning extracted gas to the liquid.

5. The system according to claim 1 comprising means for regulating the temperature of the liquid in the system.

6. The system according to claim 5, wherein the temperature regulating means comprises at least one of
   a. a heat exchanger; and
   b. a thermoelectric device.

7. The system according to claim 1 comprising means for measuring the temperature of the liquid in the system.

8. The system according to claim 1, wherein the liquid reservoir comprises an electrical transformer and the gas-containing liquid comprises a transformer oil.

9. The system according to claim 1, wherein the IR detectors detect IR light at respective ones of the following wavelengths:
   (1) 2.59 $\mu$m,
   (2) 3.32 $\mu$m,
   (3) 4.25 $\mu$m,
   (4) 4.67 $\mu$m,
   (5) 7.65 $\mu$m,
   (6) 10.6 $\mu$m, and
   (7) 13.7 $\mu$m.

10. The system according to claim 1, wherein the gas sensor comprises a thermal conductivity sensor.

11. The system according to claim 9, wherein selected ones of the IR detectors detect light at respective ones of the following wavelengths:
    a. 3.91 $\mu$m, and
    b. 9 $\mu$m.

12. The system according to claim 9, wherein the IR emitter is separated from the IR detectors in a tube by an optical path of at least one inch.

13. The system according to claim 9, wherein each IR detector comprises a broadband detector and a narrow band filter, the narrow band filter having a full width half maximum (FWHM) bandwidth of less than 0.5 $\mu$m.

14. The system according to claim 10, wherein the thermal conductivity sensor comprises a bridge circuit, the bridge circuit comprising:
    a. an electrical input;
    b. a first negative temperature coefficient (NTC) thermistor;
    c. a second NTC thermistor; and
    c. an electrical output;
    wherein the resistance of the first NTC thermistor varies as a function of the temperature of the extracted gas present in the sample chamber, the resistance of the second NTC thermistor varies as a function of the temperature of the sample chamber, and the electrical output of the thermal conductivity sensor comprises an electrical signal which is representative of the difference between the resistances of the first and second NTC thermistors.

15. The system according to claim 14, wherein the processor has an input coupled with the electrical output of the thermal conductivity sensor, the processor receiving the electrical signal corresponding to the difference between the resistances of the first and second NTC thermistors, and therefrom computing the thermal conductivity of the extracted gas and the concentration of hydrogen present in the extracted gas.

16. A sensor system for measuring the concentration of gas dissolved in a liquid, the gas comprising one or more constituent gases in a distribution, the system comprising:

a. a passive gas extractor which extracts dissolved gas from the gas-containing liquid, there being a known relationship between the concentration of a constituent gas in the extracted gas and the concentration of the constituent gas remaining dissolved in the gas-containing liquid; and b. a gas sensor which senses the concentration of a constituent gas in the extracted gas, in the presence of other constituent gases, the gas sensor comprising (1) a sample chamber which receives the extracted gas, (2) a non-dispersive infrared (IR) absorption sensing system which generates an electrical signal corresponding to the light absorption, at one or more specified IR wavelengths, of the extracted gas in the chamber, the non-dispersive IR absorption sensing system comprising an IR emitter assembly and an IR detector assembly, wherein:

a. the IR emitter assembly comprises a blackbody source which emits light from 2.5 to 15 $\mu$m; and b. the IR detector assembly comprises six IR detectors with each IR detector detecting light at a different one of the following wavelengths: 2.59 $\mu$m, 3.32 $\mu$m, 4.25 $\mu$m, 4.67 $\mu$m, 7.65 $\mu$m, 10.6 $\mu$m, and 13.7 $\mu$m; and (3) an electrical output comprising the electrical signal generated by the non-dispersive IR absorption sensing system.

17. The sensor system according to claim 16 comprising a processor having an input coupled with the electrical output of the gas sensor, the processor receiving the electrical signal corresponding to the light absorption, at the one or more specified IR wavelengths, of the extracted gas in the chamber, and therefrom computing the concentration of at least one gas constituent present in the extracted gas.

18. The system according to claim 16 comprising:

a. means for receiving a gas-containing liquid from a liquid reservoir; and b. means for returning liquid to the liquid reservoir.

19. The system according to claim 16 comprising:

a. means for passing extracted gas to the gas sensor; and b. means for returning extracted gas to the liquid.

20. The system according to claim 16 comprising means for regulating the temperature of the liquid in the system.

21. The system according to claim 20, wherein the temperature regulating means comprises at least one of a. a heat exchangerl and b. a thermoelectric device.

22. The system according to claim 16 comprising means for measuring the temperature of the liquid in the system.

23. The system according to claim 16, wherein the IR detector assembly comprises an IR detector which detects light at one of the following wavelengths:

a. 3.91 $\mu$m.; and b. 9 $\mu$m.

24. The system according to claim 16, wherein the IR detector assembly has an optical path of at least one inch.

25. The system according to claim 16, wherein the IR detector comprises a broadband detector and a narrow band filter, the narrow band filter having a full width half maximum (FWHM) bandwidth of less than 0.5 $\mu$m.

26. The system according to claim 16, wherein the gas sensor further comprises a thermal conductivity sensor.

27. The system according to claim 26, wherein the thermal conductivity sensor comprises a bridge circuit, the bridge circuit comprising:

a. an electrical input;

b. a first negative temperature coefficient (NTC) thermistor;

c. a second NTC thermistor; and c. an electrical output;

wherein the resistance of the first NTC thermistor varies as a function of the temperature of the extracted gas present in the sample chamber, the resistance of the second NTC thermistor varies as a function of the temperature of the sample chamber, and the electrical output of the thermal conductivity sensor comprises an electrical signal which is representative of the difference between the resistances of the first and second NTC thermistors.

28. The system according to claim 27, wherein the processor has an input coupled with the electrical output of the thermal conductivity sensor, the processor receiving the electrical signal corresponding to the difference between the resistances of the first and second NTC thermistors, and therefrom computing the thermal conductivity of the extracted gas and the concentration of hydrogen present in the extracted gas.

29. The system according to claim 16, wherein the liquid reservoir comprises an electrical transformer and the gas-containing liquid comprises a transformer oil.

30. The system according to claim 16, wherein the passive gas extractor comprises a permselective membrane comprising an amorphous perfluoro-2,2-dimethyl-1,3-dioxole polymer.

* * * * *